US010786539B2

(12) United States Patent
Martin et al.

(10) Patent No.: US 10,786,539 B2
(45) Date of Patent: Sep. 29, 2020

(54) USE OF ELICITED IRIDACEAE PLANT CELLS IN THE TREATMENT OF SENSITIVE SKIN

(71) Applicant: L'OREAL, Paris (FR)

(72) Inventors: Richard Martin, Rochecorbon (FR); Pascal Hilaire, Vouvray (FR)

(73) Assignee: L'OREAL, Paris (FR)

( * ) Notice: Subject to any disclaimer, the term of this patent is extended or adjusted under 35 U.S.C. 154(b) by 598 days.

(21) Appl. No.: 14/764,231

(22) PCT Filed: Jan. 29, 2014

(86) PCT No.: PCT/EP2014/051684
§ 371 (c)(1),
(2) Date: Jul. 29, 2015

(87) PCT Pub. No.: WO2014/118207
PCT Pub. Date: Aug. 7, 2014

(65) Prior Publication Data

US 2015/0366929 A1 Dec. 24, 2015

(30) Foreign Application Priority Data

Jan. 29, 2013 (FR) ..................................... 13 50758

(51) Int. Cl.

| | |
|---|---|
| ***A61K 35/744*** | (2015.01) |
| ***A61K 35/747*** | (2015.01) |
| ***A61K 36/88*** | (2006.01) |
| ***A61Q 19/00*** | (2006.01) |
| ***A61K 8/99*** | (2017.01) |
| ***A61K 8/9794*** | (2017.01) |

(52) U.S. Cl.
CPC ............ *A61K 36/88* (2013.01); *A61K 8/9794* (2017.08); *A61K 8/99* (2013.01); *A61Q 19/005* (2013.01); *A61K 2800/78* (2013.01)

(58) Field of Classification Search
None
See application file for complete search history.

(56) References Cited

U.S. PATENT DOCUMENTS

| | | | | |
|---|---|---|---|---|
| 6,019,967 | A | 2/2000 | Breton et al. | |
| 6,471,997 | B1 | 10/2002 | Breton et al. | |
| 6,682,763 | B2 * | 1/2004 | Kuno | A61K 8/0212 424/401 |
| 7,300,649 | B2 * | 11/2007 | Tanojo | A61K 8/19 424/678 |
| 8,241,613 | B2 * | 8/2012 | Candau | A61K 8/11 424/59 |
| 2002/0041908 | A1 | 4/2002 | Breton et al. | |
| 2006/0018867 | A1 * | 1/2006 | Kawasaki | A61K 8/898 424/70.122 |
| 2007/0003510 | A1 | 1/2007 | Henry et al. | |
| 2007/0122492 | A1 * | 5/2007 | Behr | A61Q 17/04 424/725 |
| 2008/0183250 | A1 * | 7/2008 | Tanojo | A61K 8/19 607/88 |
| 2010/0239621 | A1 * | 9/2010 | Tsujihata | A61K 8/0208 424/401 |

FOREIGN PATENT DOCUMENTS

| | | | |
|---|---|---|---|
| EP | 0 723 774 | A1 | 7/1996 |
| EP | 1 174 120 | A1 | 1/2002 |
| EP | 1 452 167 | A1 | 9/2004 |
| FR | 2 738 486 | A1 | 3/1997 |
| JP | 2012 116766 | A | 6/2012 |
| WO | WO-97/09056 | A1 | 3/1997 |

* cited by examiner

*Primary Examiner* — Sharmila G Landau
*Assistant Examiner* — Douglas F White
(74) *Attorney, Agent, or Firm* — Polsinelli PC

(57) ABSTRACT

This invention relates to the use of *Lactobacillus delbrueckii* to elicit a plant cell of an Iridaceae and the use of these elicited cells in treating sensitive skins.

18 Claims, No Drawings

USE OF ELICITED IRIDACEAE PLANT CELLS IN THE TREATMENT OF SENSITIVE SKIN

CROSS REFERENCE TO RELATED APPLICATIONS

This application is a National Phase filing under 35 U.S.C. § 371 of PCT/EP2014/051684 filed on Jan. 29, 2014; and this application claims priority to Application No. 1350758 filed in France on Jan. 29, 2013. The entire contents of each application are hereby incorporated by reference.

This invention relates to the cosmetic or pharmaceutical treatment of sensitive skin and disorders associated with an excessive synthesis and/or release of calcitonin derived peptide (known as Calcitonin Gene Related Peptide or CGRP).

CGRP is a polypeptide chemical element produced and released by a nerve ending. As the location of CGRP is specific of sensitive nerve fibers (C fibers), numerous organs or tissues receive afferent neurons to CGRP, such as the salivary glands, stomach, pancreas, intestine, the cardiovascular system, thyroid gland or the skin.

Through this ubiquitous distribution of CGRP, numerous disorders are associated with an excessive synthesis and/or release of CGRP. This is the case in particular of respiratory and inflammatory diseases, allergic diseases and skin disorders such as dermatological conditions including eczema, prurigo or rosacea.

The use of CGRP antagonists is an effective treatment in all the diseases mentioned hereinabove.

Moreover, the Applicant has shown that one of the essential characteristics of sensitive skins was linked to the release of CGRP. Consequently, the use of CGRP antagonists can also be used to obtain a preventive and/or curative treatment of sensitive skins.

"CGRP antagonist" means here any compound capable of inhibiting partially or even completely, the biological effect of CGRP.

Among the known CGRP antagonists that may be mentioned for example CGRP 8-37 (sequence of amino acids 8 to 37 of the N-terminal part of CGRP) or anti-CGRP antibodies.

Moreover, the Applicant has shown in application FR 2738486 that an extract of at least one Iridaceae was able to reduce the vasodilation induced by capsaicin and/or by an antidromic electrical stimulation (applied to an afferent nerve) and/or cause inhibition of the release of CGRP by sensitive nerve fibers and/or cause an inhibition of the contraction of smooth muscle of the vas deferens induced by CGRP, and could therefore be used as a CGRP antagonist, in particular for treating the diseases mentioned above and sensitive skins.

However, this extract did not make it possible to inhibit CGRP partially, by about 70%.

There is therefore still a substantial need for compositions that have more substantial CGRP antagonist activity.

Moreover, the extract described in application FR 2738486 could contain harmful compounds with regards to the antagonist activity of the CGRP and the molecules responsible for this antagonistic activity were not excreted in the culture medium, reducing therefore the productivity of the culture.

There is therefore still a substantial need for compositions that have CGRP antagonist activity that can be obtained with high productivity.

This invention results from the unexpected discovery, by the inventors, that an extract of *Lactobacillus delbrueckii* spp *lactis* acts as elicitor on *iris* plant cells. Indeed, when it is added to a culture of *iris* dedifferentiated cells, this extract allows an overexpression of the CGRP antagonist activity both intracellular and extracellular of the *iris* cells, inducing maximized inhibition of CGRP, of about 100%. Furthermore, the excretion, in the external environment, of the molecules responsible for this antagonistic activity makes it possible to significantly increase the productivity of the culture.

This invention therefore relates to the use of *Lactobacillus delbrueckii* to elicit a plant cell of an Iridaceae.

It also relates to the use of *Lactobacillus delbrueckii* to induce the production of an antagonist of CGRP by a plant cell of an Iridaceae.

This invention also relates to a method for elicitation of plant cells of an Iridaceae comprising placing plant cells of an Iridaceae in contact with *Lactobacillus delbrueckii* under conditions suitable to induce the expression of a CGRP antagonist activity.

It also relates to a method of preparing a composition having a CGRP antagonist activity comprising the steps consisting in:

a) placing in contact, in a culture medium, the plant cells of an Iridaceae with *Lactobacillus delbrueckii* under conditions suitable to induce expression of a CGRP antagonist activity,
b) optionally separating plant cells cultivated in step a) from the culture medium, and
c) recovering a composition with CGRP antagonist activity.

This invention also relates to a composition having a CGRP antagonist activity of that can be obtained by this preparation method.

It also has for object a cosmetic composition comprising a composition having antagonist activity of CGRP that can be obtained by this preparation method, and a cosmetically acceptable carrier.

Another object of this invention relates to the use of this cosmetic composition for treating sensitive skins or in anti-dandruff treatment.

This invention further relates to a composition having a CGRP antagonist activity that can be obtained by the preparation process hereinabove for use in the treatment of disorders associated with an excessive synthesis and/or release of CGRP.

DETAILED DESCRIPTION OF THE INVENTION

CGRP Antagonist Activity

In the context of the invention, the term "peptide derivative of calcitonin" "Calcitonin Gene Related Peptide" or "CGRP" refers to a peptide member of the family of the calcitonin produced in the central and peripheral neurons and which exists, in humans in two forms, α-CGRP and β-CGRP. CGRP acts via a heteromeric receptor comprising a receptor coupled to a G protein, known as "calcitonin receptor-like receptor" or CALCRL, and a protein modifying the activity of the receptor or RAMP.

"CGRP antagonist" means here any compound capable of inhibiting partially or even completely, the biological effect of CGRP. Preferably, an antagonist of CGRP or a compound having antagonist activity of CGRP according to the invention is capable of producing an inhibition of the receptor binding of CGRP or of effecting inhibition of the synthesis and/or release of CGRP by nerve sensory fibers. Particularly preferably, an antagonist of CGRP or a compound having antagonist activity of CGRP according to the invention is capable of producing an inhibition of the receptor binding of CGRP. Even more preferably, an antagonist of CGRP or a compound having antagonist activity of CGRP according to the invention has an affinity for CGRP receptors.

Extract from *Lactobacillus delbrueckii*

"*Lactobacillus delbrueckii*" here means a Gram-positive bacterium of the genus *Lactobacillus*, non-mobile, capable of fermenting carbohydrate substrates into lactic acid under anaerobic conditions. As is well known to those skilled in the art, the species *Lactobacillus delbrueckii* includes 4 subspecies: *Lactobacillus delbrueckii* spp *bulgaricus, Lactobacillus delbrueckii* spp *lactis, Lactobacillus delbrueckii delbrueckii* and *Lactobacillus delbrueckii indicus.*

Preferably, the subspecies of *Lactobacillus delbrueckii* used as part of the invention is *Lactobacillus delbrueckii lactis. Lactobacillus delbrueckii lactis* spp includes in particular the strains ATCC 4797, DSM 20076, NCDO 299, NCIB 7854, DSM 7290 and NCC 88. Preferably, the strain of *Lactobacillus delbrueckii lactis* spp used in the context of the invention is the strain ATCC 4797.

The bacterium *Lactobacillus delbrueckii* used in the framework of the invention can be implemented in a live, semi-active, inactivated or dead form. Preferably, the bacterium *Lactobacillus delbrueckii* is implemented in inactivated or dead form.

In the sense of the invention, an "inactivated" micro-organism is a micro-organism which is no longer capable, temporarily or definitively, of forming colonies in culture.

In the sense of the invention, a "dead" micro-organism is a micro-organism which is no longer capable, definitively, of forming colonies in culture. Dead or inactivated micro-organisms may have intact or ruptured cell membranes. As such, the term "inactivated" also denotes the micro-organism extracts and lysates as detailed hereinafter. Dead or inactivated micro-organisms may be obtained by any method known to those skilled in the art.

According to an advantageous embodiment, the bacteria *Lactobacillus delbrueckii* implemented according to the invention are at least in part inactivated or dead.

"*Lactobacillus delbrueckii*" at least partially inactivated" means a preparation of *Lactobacillus delbrueckii* bacteria in accordance with the invention comprising at least 80%, in particular at least 85%, more particularly at least 90% or at least 95%, or at least 99% of bacteria *Lactobacillus delbrueckii* inactivated expressed as colony forming unit (cfu) with respect to all bacteria *Lactobacillus delbrueckii* not inactivated live contained in the initial preparation prior to being subjected to an inactivation method. The inactivation rate obtained is dependent on the application conditions of the inactivation method which are adjusted by those skilled in the art according to the inactivation rate to be obtained. According to one embodiment, the invention comprises the implementation of a preparation comprising 100% inactivated *Lactobacillus delbrueckii* bacteria.

*Lactobacillus delbrueckii* inactivated bacteria suitable for the invention may be prepared by irradiation, heat inactivation or lyophilization of a preparation of *Lactobacillus delbrueckii* bacteria. These methods are known to those skilled in the art.

*Lactobacillus delbrueckii* bacteria according to the invention may be used in whole form, i.e. essentially in the native form thereof, or in the form of extracts or lysates comprising fractions and/or metabolites of these bacteria.

Within the meaning of the invention, the term "fraction" refers to a fragment of said bacterium with an efficiency elicitation by analogy to said whole bacterium.

In the sense of the invention, the term "metabolite" denotes any substance derived from the metabolism of the bacteria, and in particular secreted by the bacteria considered according to the invention and also provided with an efficiency elicitation.

An extract or a lysate suitable for the invention may be prepared using bacteria, at the end of the growth phase.

According to a preferred embodiment, the bacterium *Lactobacillus delbrueckii* suitable for the invention can be prepared in the form of an extract.

A extract in the sense of the invention commonly denotes a material obtained following the destruction or dissolution of biological cells by a phenomenon referred to as cell lysis thus inducing the release of the intracellular biological constituents naturally contained in the cells of the micro-organism considered. In the sense of the present invention, the term "extract" is used equally to denote the entire lysate obtained by lysis of the micro-organism in question or merely a fraction thereof. The extract used is thus formed completely or partially of the intracellular biological constituents and the constituents of the cell walls and membranes of the bacterium *Lactobacillus delbrueckii*. Advantageously, an extract used for the invention can be all of the extract obtained by lysis of the bacterium *Lactobacillus delbrueckii.*

This cellular lysis may be carried out using different technologies, such as for example an osmotic shock, thermal shock, by ultrasound, or under mechanical stress such as centrifugation or pressure.

More particularly, this extract may be obtained according to the following protocol: the extract is obtained by passing a medium comprising *Lactobacillus delbrueckii* bacteria in a French press, preferably followed by cascade filtrations, and preferably a lyophilization.

An extract may be implemented in various forms, such as in the form of a solution or in a powder form.

The inventors have shown in particular an extract of *Lactobacillus delbrueckii* spp *lactis* obtained by the technique described hereinabove, acted as an elicitor on *iris* plant cells, while other Gram-positive bacteria did not have this property.

Plant Cell Iridaceae

The Iridaceae family (or Iridescent) has about 750 species. The plants of this family are mainly used for their aromatic and ornamental properties.

Among the kinds of Iridaceae which plant cells are used in the framework of the invention include for example the genera *Romulea, Crocus, Iris, Gladiolus, Sisyrinchium* and *Hermodactylus*. Preferably, the plant cells used in the framework of the invention are plant cells from *iris.*

Plant cells used within the framework of the invention can more particularly be from *Iris germanica, Iris florentina, Iris pallida, Crocus versicolor, Romulea bulbucodium* or *Gladiolus communis*. Preferably, the plant cells used in the framework of the invention are derived from *Iris pallida.*

Particularly preferably, the plant cell used in the framework of the invention is a dedifferentiated cell of an Iridaceae, such as defined hereinabove.

"Dedifferentiated plant cell" here means any plant cell that does not have any of the characters of a specific specialization and capable of living by itself and not in dependence with other cells. These dedifferentiated plant cells are optionally capable, under the effect of an induction, of any differentiation in accordance with their genome.

Plant cells used in the framework of the invention are preferably plant cells cultivated in vitro.

The selection pressure imposed by the physical-chemical conditions during the cultivation of plant cells in vitro makes it possible to obtain a standardized plant material available throughout the year, unlike the plants cultivated in vivo.

Method of Elicitation

This invention relates to the use of *Lactobacillus delbrueckii*, more particularly an extract of *Lactobacillus delbrueckii*, such as defined in the "*Lactobacillus delbrueckii*" section hereinabove, to elicit a plant cell of an Iridaceae, as defined in the "Plant Cell Iridaceae" section hereinabove.

It also relates to a method of elicitation of plant cells of an Iridaceae comprising the putting into contact of plant cells of an Iridaceae, such as defined in the "Plant Cell Iridaceae" section hereinabove, with *Lactobacillus delbrueckii*, preferably with an extract of *Lactobacillus delbrueckii* spp *lactis* as defined in the "*Lactobacillus delbrueckii*" section herein above, under conditions suitable to induce the expression of a CGRP antagonist activity such as defined in the "CGRP Antagonist" section hereinabove.

"Elicitation" here means the act of inducing, by exogenous elicitor, in another organism or cell, a metabolic pathway with little expression or to waken, in another organism or cell, silent metabolic pathways.

Preferably, "elictation" here means the stimulation by an exogenous elicitor, the CGRP antagonist activity such as defined in the "CGRP Antagonist" section hereinabove, in another organism or cell.

"Elicitors" here means the molecules or organisms that are capable of inducing, in another organism, a metabolic pathway with little expression or to waken, in another organism or cell, silent metabolic pathways. A large number of elicitors are known to those skilled in the art and include biotic elicitors, such as jasmonate and its derivatives, and abiotic elicitors such as temperature, pH or osmotic shock.

"Putting in contact" here means incubating, in the same culture medium plant cells and the bacterium *Lactobacillus delbrueckii*, particularly the extract of *Lactobacillus delbrueckii*.

"Appropriate conditions to induce expression of a CGRP antagonist activity" here means the conditions of time and temperature, and/or a concentration of bacterium *Lactobacillus delbrueckii*, that make it possible to induce the expression of an activity CGRP antagonist such as defined in the "CGRP Antagonist" section hereinabove, preferably making it possible to induce the expression of a CGRP agonist activity causing inhibition of more than 80%, preferably more than 90%, more preferably 95%, 96%, 97%, 98%, 99%, most preferably 100% of the CGRP receptor. Such conditions can be determined by those skilled in the art by routine techniques.

Indeed, the techniques for determining the expression of a CGRP antagonist activity are well known to those skilled in the art and are described for example in "Calcitonin gene-related peptide (CGRP) and Its role in hypertension," Sarah-Jane Smillie, Susan D. Brain. BHF Centre of Cardiovascular Excellence and Centre for Integrative Biomedicine, Cardiovascular Division, Franklin-Wilkins Building, Waterloo Campus, King's College London, London SE1 9NH, UK.

Typically, the expression of CGRP antagonist activity can be demonstrated as follows: transfected HEK cells stably by the receiver hCALCRL and associated protein hRAMPI and expressing the reporter gene for β-lactamase under the control of the response element in the cyclic AMP (CRE) are cultured, preferably in DMEM+serum, at 37° C. and 5% $CO_2$. The cells are then treated with the reference ligand CGRP, e.g. to its EC80 (typically 0.2 nM final) and different doses of candidate compositions. After incubation, preferably between 2 and 4 hours, for example 3 hours, of incubation at 37° C. 5% $CO_2$, the substrate of β-lactamase is added. After incubation, for example for 2 hours, typically at room temperature, the degradation of the substrate of β-lactamase is measured, for example using a spectrophotometer.

Preferably, in the method of elicitation according to the invention, the plant cells of an Iridaceae, such as defined in the "Plant Cell Iridaceae" section hereinabove, are placed in contact with *Lactobacillus delbrueckii*, preferably with an extract of *Lactobacillus delbrueckii* spp *lactis* such as defined in the "*Lactobacillus delbrueckii*" section hereinabove, at a concentration of 200 μg of extract/liter of culture for 7 days at a temperature of 26° C.

Preparing a Composition Having CGRP Antagonist Activity

This invention also relates to the use of *Lactobacillus delbrueckii*, preferably an extract of *Lactobacillus delbrueckii*, such as defined in the "*Lactobacillus delbrueckii*" section hereinabove, to induce the production of a CGRP antagonist, such as defined in the "CGRP Antagonist" section hereinabove, by a plant cell of an Iridaceae, such as defined in the "Plant Cell Iridaceae" section hereinabove.

This invention also relates to a method of preparing a composition having antagonist activity of CGRP comprising the steps consisting in:

a) putting into contact, in a culture medium, plant cells of an Iridaceae, such as defined in the "Plant Cell Iridaceae" section hereinabove, with *Lactobacillus delbrueckii*, preferably with an extract of *Lactobacillus delbrueckii* such as defined in the "*Lactobacillus delbrueckii*" section herein above, under conditions suitable to induce the expression of a CGRP antagonist activity, such as defined in the "Method of elicitation" section hereinabove, b) optionally separating plant cells cultivated in step a) from the culture medium, and c) recovering a composition with CGRP antagonist activity.

"Putting in contact" here means incubating, in the same culture medium plant cells and the bacterium *Lactobacillus delbrueckii*, particularly the extract of *Lactobacillus delbrueckii*.

"Culture medium" here means a solution comprising all the necessary nutrients for plant cells for their survival and growth. Such culture media are well known to those skilled in the art and are for example described in "Plant Culture Media: Formulation and Uses, Edwin F. George, David J. M. Puttock and Heather J. George". Examples of suitable culture media for the implementation of the invention include the medium described in Murashige and Skoog (1962) Physiol. Plant. 15: 473-497.

"Appropriate conditions to induce expression of CGRP antagonist activity" here means the same conditions as those described in the "Method of elicitation" section hereinabove.

Any conventional separation technique can be used to separate the plant cells from the culture medium in optional step b). Such techniques include for example, centrifugation, filtration or decantation.

"Composition with CGRP antagonist activity" here means a mixture comprising molecules having a CGRP antagonist activity such as defined in the "CGRP antagonist" section hereinabove, produced by the plant cells following putting them in contact with *Lactobacillus delbrueckii* in step a) of the process according to the invention. Such a composition can therefore contain compounds other than those having antagonist activity of CGRP, particularly other compounds from the plant cell and/or *Lactobacillus delbrueckii* and/or the culture medium.

The nature of the molecules with this CGRP antagonist activity has not yet been determined. However, it has been demonstrated by the Applicant that these molecules having antagonistic activity are only expressed by the cultured plant cells, and not by *Lactobacillus delbrueckii*.

In a particular embodiment of the invention, the composition having a CGRP antagonist activity recovered in step c) is an extract of plant cells separated in stage b).

Any extraction method known to those skilled in the art can be used to obtain an extract of the plant cells separated in stage b). Particular mention can be made of alcoholic extracts, especially ethanolic or hydroalcoholic extracts. The extract of plant cells can also be an aqueous extract, typically prepared by resuspending the separated plant cells in osmosed water, preferably in an amount equivalent to the volume of the starter culture, preferably followed by a passing high pressure homogenizer (HPH) typically at 1250 Bar, centrifugation, preferably at 6000 g for 20 min at 4° C., filtration, for example on thick filter as FGD® filter and/or on GFF filter ("Gravity fiber flow"), and freezing, for example at −20° C.

The Applicant has demonstrated that the putting in contact of *Lactobacillus delbrueckii* made it possible to induce secretion into the external environment of the molecules responsible for the antagonistic activity of CGRP produced by plant cells.

In a particular embodiment of the invention, the composition having a CGRP antagonist activity recovered in step c) is therefore after the culture medium separated in step b). This culture medium can be lyophilized, spray-dried or concentrated as is or undergo a fractionation on a molecular sieve of the tangential filtration type then be processed according to the techniques described hereinabove.

In another particular embodiment of the invention, the method of preparing a composition having antagonist activity of CGRP does not include a step of separating plant cells cultivated in step a) of the culture medium, and the composition having a CGRP antagonist activity recovered in step c) therefore includes both the culture medium and cultured plant cells and elicited in step a).

"Composition with CGRP antagonist activity" here means a mixture comprising molecules having a CGRP antagonist activity such as defined in the "CGRP antagonist" section hereinabove, produced by the plant cells following putting them in contact with *Lactobacillus delbrueckii* in step a) of the process according to the invention. Such a composition can therefore contain compounds other than those having antagonist activity of CGRP, particularly other compounds from the plant cell and/or *Lactobacillus delbrueckii* and/or the culture medium.

This invention therefore also relates to a composition having antagonist activity of CGRP that can be obtained, preferably obtained, by the preparation method according to the invention described hereinabove. Preferably, this composition with antagonist activity of CGRP comprises compounds coming from *Lactobacillus delbrueckii*.

The nature of the molecules with this CGRP antagonist activity has not yet been determined. However, it has been demonstrated by the Applicant that these molecules having antagonistic activity are only expressed by the cultured plant cells, and not by *Lactobacillus delbrueckii*.

Cosmetic and Pharmaceutical Composition

This invention also relates to a cosmetic or pharmaceutical composition comprising a composition having a CGRP antagonist activity such as defined in the "Preparation of a composition having a CGRP antagonist activity" section hereinabove and a cosmetically or pharmaceutically acceptable carrier.

The term "cosmetically acceptable carrier" denotes herein a medium having no unpleasant odor or appearance, and not giving rise to stinging, tautness or redness unacceptable for the user, during the administration thereof, particularly during the topical application thereof on the skin and skin appendages.

"Pharmaceutically acceptable carrier" herein means any solvent, dispersion medium, absorption delaying agents, etc., which produces no side reaction, for example allergic, in humans or animals. Pharmaceutically acceptable carriers are well known to those skilled in the art, and include those described in "Remington's Pharmaceutical Sciences" (Mack Publishing Company, Easton, USA, 1985).

The cosmetically or pharmaceutically acceptable carrier will be suitable for the administration route of the cosmetic or pharmaceutical composition, particularly for the nature of the substrate whereon the cosmetic or pharmaceutical composition is to be applied, as well as to the form under which the cosmetic or pharmaceutical composition is intended to be packaged, notably solid or fluid at ambient temperature and atmospheric pressure.

According to the invention, the composition having antagonist activity of CGRP, such as defined in the "Preparation of a composition having antagonist activity of CGRP" section hereinabove, is used in an amount representing from 0.001% to 20% of total weight of the cosmetic or pharmaceutical composition, and preferably in an amount representing from 0.1% to 10% of the total weight of the cosmetic or pharmaceutical composition.

The cosmetic or pharmaceutical composition of the invention may be ingested, injected or applied to the skin (to any skin area of the body), hair, nails or mucous membranes (buccal, jugal, gingival, genital, conjunctiva). Depending on the mode of administration, the cosmetic or pharmaceutical composition according to the invention may be in any dosage form normally used.

For topical application to the skin, the cosmetic or pharmaceutical composition according to the invention may take the form in particular of an aqueous or oily solution or dispersion of the lotion or serum type, emulsions of liquid or semi-liquid consistency of the milk type, obtained by dispersing a fatty phase in an aqueous phase (O/W) or conversely (W/O), or suspensions or emulsions of soft type cream or aqueous or anhydrous gel type, or alternatively microcapsules or microparticles, or vesicular dispersions of ionic and/or nonionic surfactant. These cosmetic or pharmaceutical compositions are prepared according to routine methods.

They can also be used for the hair in the form of aqueous, alcoholic or hydroalcoholic solutions, or in the form of creams, gels, emulsions or mousses, or alternatively in the form of aerosol compositions also comprising a propellant under pressure.

For injection, the cosmetic or pharmaceutical composition according to the invention may be in the form of aqueous or oily lotion or in serum form. For the eyes, it may be in the form of drops, and for ingestion, it can be in the form of capsules, granules, syrups or tablets.

The amounts of the various constituents of the cosmetic or pharmaceutical compositions according to the invention are those conventionally used in the fields considered.

These compositions constitute in particular cleansing creams, protection, treatment or care for the face, hands, feet, for the major anatomical folds or for the body (for example day creams, night creams, cleansing, foundation creams complexion, sunscreen creams), fluid foundations, makeup-removing milks, body milks for protection or care, sunscreen milks, lotions, gels or foams for skin care, as cleansing lotions, sunscreen lotions, artificial tanning lotions, bath compositions, deodorant compositions comprising a bactericidal agent, aftershave gels or lotions, depilatory creams, compositions against insect bites, of anti-pain compositions, compositions for treating certain skin diseases such as eczema, ulcers of the leg, rosacea, psoriasis, lichens and severe pruritus, pustules, or stretch marks.

The cosmetic or pharmaceutical compositions according to the invention may also consist of solid preparations constituting soaps or cleansing bars.

The cosmetic or pharmaceutical compositions according to the invention may also be packaged in the form of an aerosol composition also comprising a pressurized propellant.

The composition having a CGRP antagonist activity used according to the invention can also be incorporated into various compositions for hair care, and in particular shampoos, hair setting lotions, treating lotions, styling creams or gels, compositions dyes (especially oxidation dyes) optionally in the form of coloring shampoos, restructuring lotions for hair, permanent wave compositions (especially compositions for the first stage of a permanent wave), lotions or gels for combating hair, antiparasitic shampoos, etc.

The cosmetic or pharmaceutical compositions according to the invention may also be in oral use, for example a toothpaste. In this case, they may contain conventional adjuvants and additives for the oral compositions including surfactants, thickeners, humectants, polishing agents such as silica, various active ingredients such as fluorides, especially sodium fluoride, and optionally sweetening agents such as sodium saccharinate.

When the cosmetic or pharmaceutical composition according to the invention is an emulsion, the proportion of the fatty phase may range from 5 to 80% by weight, and preferably from 5 to 50% by weight relative to the total weight of the composition. The oils, waxes, emulsifiers and co-emulsifiers used in the composition in emulsion form are chosen from those conventionally used in the cosmetic field. The emulsifier and the coemulsifier are present preferably in the cosmetic or pharmaceutical composition, in an amount ranging from 0.3% to 30% by weight, and more preferably from 0.5 to 20% by weight relative to the total weight of the cosmetic or pharmaceutical composition. The emulsion may further contain lipid vesicles.

When the cosmetic or pharmaceutical composition according to the invention is an oily gel or solution, the fatty phase may represent more than 90% of the total weight of the cosmetic or pharmaceutical composition.

In a known manner, the cosmetic composition may also contain usual additives in the cosmetic field, such as hydrophilic or lipophilic gelling agents, hydrophilic or lipophilic additives, preservatives, antioxidants, solvents, perfumes, bulking agents, filters, odor absorbers and dyes. The quantities of these various additives are conventionally the quantities used in the cosmetic field, for example from 0.01 to 10% of the total weight of the cosmetic composition. These additives, depending on their nature, may be introduced in the fatty phase in the aqueous phase and/or in lipid spheres.

As oils or waxes that can be used in the invention, mention can be made of mineral oils (vaseline oil), vegetable oils (liquid fraction of shea butter, sunflower oil), animal oils (perhydrosqualene), synthetic oils (Purcelin oil), silicone oils or waxes (cyclomethicone) and fluorinated oils (perfluoropolyethers), beeswax, carnauba wax or paraffin. Can be added to these oils fatty alcohols and fatty acids (stearic acid).

As emulsifiers that can be used in the invention, mention can be made of for example glycerol stearate, polysorbate 60 and the PEG-6/PEG-32/glycol stearate sold under the name Tefose® 63 by Gattefosse.

As solvents that can be used in the invention, mention may be made of lower alcohols, particularly ethanol and isopropanol, propylene glycol.

As hydrophilic gelling agents that can be used in the invention, mention can be made of carboxyvinyl polymers (carbomer), acrylic copolymers such as acrylate/alkylacrylate copolymers, polyacrylamides, polysaccharides such as hydroxypropyl cellulose, natural gums and clays, and lipophilic gelling agents include modified clays such as bentones, metal salts of fatty acids such as aluminum stearates and hydrophobic silica, ethylcellulose and polyethylene.

The cosmetic composition according to the invention may contain other hydrophilic active agents such as proteins or protein hydrolysates, amino acids, polyols, urea, allantoin, sugars and sugar derivatives, water-soluble vitamins, plant extracts and hydroxy acids.

As lipophilic active agents, mention can be made of retinol (vitamin A) and its derivatives, tocopherol (vitamin E) and its derivatives, essential fatty acids, ceramides, essential oils, salicylic acid and its derivatives.

According to the invention, it is possible, inter alia, to combine at least one composition having a CGRP antagonist activity such as defined in the "Preparation of a composition having antagonist activity of CGRP" section hereinabove for other active agents intended in particular for the prevention and/or treatment of skin disorders Among these active agents, mention can be made for example of:

- agents modulating skin differentiation and/or proliferation and/or pigmentation, such as retinoic acid and its isomers, retinol and its esters, vitamin D and its derivatives, estrogens such as estradiol, the kojic acid or hydroquinone;
- antibacterials such as clindamycin phosphate, erythromycin or antibiotics of the tetracycline class;
- anti-parasites, in particular metronidazole, crotamiton or pyrethroids;
- antifungal agents, in particular compounds belonging to the imidazole class, such as econazole, ketoconazole or miconazole or their salts, polyene compounds, such as amphotericin B, compounds of the allylamine family, such as terbinafine;
- antiviral agents such as acyclovir;
- anti-inflammatory agents, particularly steroidal anti-inflammatory agents such as hydrocortisone, betamethasone valerate or clobetasol propionate, or non-steroidal anti-inflammatory agents such as ibuprofen and its salts, diclofenac and its salts, acetylsalicylic acid, acetaminophen or glycyrrhetinic acid;

anesthetics such as lidocaine hydrochloride and its derivatives;

antipruritic agents such as thenaldine, trimeprazine or cyproheptadine;

keratolytic agents such as alpha- and beta-hydroxycarboxylic acids or beta-ketocarboxylic acids, their salts, amides or esters and more particularly hydroxyacids, such as glycolic acid, lactic acid, salicylic acid, citric acid and generally fruit acids, and n-octanoyl-5-salicylic acid;

free-radical or free radical scavengers, such as alpha-tocopherol or its esters, superoxide dismutases, certain metal chelating agents or ascorbic acid and its esters;

the soothing agents such as filamentous bacteria or extracts of filamentous bacteria as *Vitreoscilla filiformis* as described in EP 761 204 and marketed by Chimex under the name Mexoryl SBG®;

anti-seborrheic agents such as progesterone;

anti-dandruff agents such as octopirox or zinc pyrithione;

anti-acne agents such as retinoic acid or benzoyl peroxide;

vitamins and derivatives or precursors thereof, alone or in mixtures;

anti-oxidant agents;

hydrophilic UV screening or insoluble in water and oils;

inorganic UV filters;

self-tanning agents;

anti-glycation agents;

NO synthase inhibitors;

agents for stimulating the synthesis of dermal or epidermal macromolecules and/or preventing their degradation;

agents for stimulating fibroblast proliferation;

agents for stimulating keratinocyte proliferation;

dermo-relaxing agents;

tightening agents;

matting agents;

desquamating agents;

moisturizing agents;

agents acting on the energy metabolism of cells;

insect repellents;

substance P antagonists;

anti-wrinkle agents;

anti-photoaging agents;

coloring agents;

pearlescent agents; and pigments.

As such, according to a particular embodiment, the invention relates to a cosmetic or pharmaceutical composition comprising a composition having a CGRP antagonist activity as defined in the "Preparation of a composition having antagonist activity of CGRP" section hereinabove, a cosmetically or pharmaceutically acceptable carrier, and at least one agent chosen from antibacterial, antiparasitic, antifungal, antiviral, anti-inflammatory, antipruritic, anesthetic, keratolytic, anti-free radicals, soothing, anti-seborrheic, dandruff, acne and/or agents modulating skin differentiation and/or proliferation and/or pigmentation.

Cosmetic Use

The Applicant has demonstrated that one of the essential characteristics of sensitive skins was linked to the release of CGRP and therefore the use of compositions having a CGRP antagonist activity could afford to obtain a preventive and/or curative treatment of sensitive skins.

The present invention therefore relates to the use of a cosmetic composition as defined in the "Cosmetic or pharmaceutical composition" section hereinabove for treating sensitive skins.

As recalled in European application EP 0723774, sensitive skin can be divided into two major clinical forms, irritable and/or reactive skins and intolerant skins.

An irritable and/or reactive skin is a skin which reacts by pruritus, that is to say by itching or stinging, to various factors such as the environment, emotions, foods, wind, friction, shaving, soap, surfactants, hard water with a high calcium concentration, temperature variations or wool. In general, these signs are associated with a dry skin with or without sores or with skin that exhibits erythema.

An intolerant skin is a skin which reacts by sensations of heating, tautness, tingling and/or redness, to various factors such as the environment, emotions, foods. In general, these signs are associated with a hyperseborrheic or acneic skin with or without sores, and with an erythema.

Moreover, in certain anatomical regions such as the major folds (groin, genital, axillary, popliteal, anal, submammary, elbow creases) and feet, sensitive skin is reflected by pruriginous sensations and/or dysaesthetic sensations (heating, stinging) associated in particular with sweat, rubbing, wool, surfactants, hard water with a high calcium concentration and/or temperature variations.

The Applicant has shown that a cosmetic composition comprising a composition having a CGRP antagonist activity as defined in the "CGRP antagonist" section hereinabove would avoid irritation and/or dysaesthetic sensations and/or pruritus of the skin and/or mucous membranes and/or erythema.

More precisely, the invention makes it possible to treat symptoms of neurogenic origin, due to an exogenous agent able to change the biophysical and biochemical constants of the affected tissue (skin, mucous membranes).

Moreover, sensitive skin is skin that reacts more easily than others to external factors. Irritation of sensitive skin begins by subjective symptoms (tingling, warm, etc.) before reaching inflammation.

This invention therefore also relates to the use, in particular cosmetic, of a cosmetic composition such as defined in the "Cosmetic or pharmaceutical composition" section hereinabove for preventing and/or combating against skin irritations and/or sores and/or erythemas and/or sensations of overheating and/or of dysesthesia and/or pruritus of the skin and/or mucous membranes.

"Sensitive" scalps have a more univocal clinical semiology: the sensations of pruritus and/or tingling and/or inflammation are essentially triggered by local factors such as rubbing, soap, surfactants, hard water with a high calcium concentration, shampoos or lotions. These sensations are also sometimes triggered by factors such as the environment, emotions and/or food. Erythema and hyperseborrhea of the scalp as well as dandruff are frequently observed in individuals with such a "sensitive" scalp.

This invention therefore also relates to the use, in particular cosmetic, of a cosmetic composition as defined in the "Cosmetic or pharmaceutical composition" section hereinabove in the anti-dandruff treatment.

This invention also relates to a non-therapeutic method of cosmetic treatment of sensitive skin, wherein there is applied to the skin, to the scalp and/or mucous membranes, a cosmetically effective amount of a cosmetic composition such as defined in the "Cosmetic or pharmaceutical composition" section hereinabove.

This invention also has for object a method for treating dandruff, wherein applying to the scalp a cosmetically effective amount of a cosmetic composition as defined in the "Cosmetic or pharmaceutical composition" section hereinabove.

The term "cosmetically effective quantity" denotes herein a sufficient quantity of the agents used within the framework of the invention in order to treat and/or prevent said cosmetic disorder, which does not induce unacceptable side-effects for the user.

Cosmetic treatment of the methods of the invention can be implemented notably by applying the cosmetic compositions such as defined in "Cosmetic or pharmaceutical composition" section hereinabove, by the usual technique of these compositions. For example: application of creams, gels, serums, lotions, makeup-removing milks or after-sun compositions on the skin or dry hair, application of a hair lotion to wet hair, shampoos or application of toothpaste to the gums.

Therapeutic Use

Through the ubiquitous distribution of CGRP, numerous disorders are associated with an excessive synthesis and/or release of CGRP. This is the case in particular of respiratory and inflammatory diseases, allergic diseases and skin disorders such as dermatological conditions including eczema, prurigo or rosacea.

This invention further relates to a composition having a CGRP antagonist activity, such as defined in the "Preparation of a composition having antagonist activity of CGRP" section hereinabove, for use in the treatment of disorders associated with an excessive synthesis and/or release of CGRP.

It also relates to the use of a composition having antagonist activity of CGRP, such as defined in the "Preparation of a composition having antagonist activity of CGRP" section hereinabove, for the manufacture of a pharmaceutical composition for treating disorders associated with an excessive synthesis and/or release of CGRP.

It also relates to a method of treating disorders associated with an excessive synthesis and/or CGRP release in a subject, wherein administering in a subject in need thereof, a therapeutically effective amount of a pharmaceutical composition such as defined in the "Cosmetic or pharmaceutical composition" section hereinabove.

"Therapeutically effective amount" herein means a sufficient amount of the agents used in the framework of the invention for treating and/or preventing said disease, with a benefit/risk ratio that is acceptable for any medical treatment. It will however be understood that the specific therapeutically effective dose for a particular patient will depend upon a variety of factors including the condition to be treated, the severity of the disease, the activity of specific agents employed, the specific composition employed, the duration of treatment, age, weight and condition of the subject treated, as well as analogous factors well known in the medical field.

Disorders associated with an excessive synthesis and/or release of CGRP are in particular selected from the group consisting of respiratory and inflammatory diseases, allergic diseases and dermatological diseases such as eczema, prurigo, rosacea, pruritis severe acne, leg ulcers, psoriasis, pimples and stretch marks.

Preferably, the disorder associated with an excessive synthesis and/or release of CGRP treated in the framework of the invention is a dermatological disease such as eczema, prurigo, rosacea, severe pruritus, acne, leg ulcers, psoriasis, pimples and stretch marks. More preferably, the disorder associated with an excessive synthesis and/or release of CGRP treated in the framework of the invention is selected from the group consisting of eczema, prurigo and rosacea. Most preferably of all, the disorder associated with an excessive synthesis and/or release of CGRP treated as part of the invention is rosacea.

In the description and in the examples hereinafter, unless specified otherwise, the percentages are percentages by weight and the value ranges worded as "between . . . and . . . " include the upper and lower limits specified.

EXAMPLES

Example 1: Preparation of the Elicitor

This example shows a method for preparing an extract of *Lactobacillus delbrueckii* spp *lactis* that can be used to implement the invention.

*Lactobacillus delbrueckii* spp *lactis* is cultured on a conventional medium called traditional MRS.

Fully grown, the cells are subjected to a passage in the French Press. After filtering in cascade, the extract is lyophilized.

Example 2: Preparation of Extracts of *Iris* Dedifferentiated Plant Cells

This example shows a method for preparing an extract of *iris* dedifferentiated plant cells that can be used to implement the invention.

a) Culture of *Iris* Dedifferentiated Plant Cells

Culture medium: Murashige & Skoog Naphthalene Acetic Acid (NAA) and 2 Kinetin 0.6, sucrose 20 g/l.

Erlenmeyer Culture: Culture volume of 400 mL Culturing is carried out at 26° C., stirring 100 rpm for 15 days.

Culture in a fermenter of 10 L: 10 effective liters in fermentor, unregulated pH, $pO_2$ 15% controlled by air. The culture is carried out at 26° C. with shaking at 100 rpm (Rushton).

In 14 days of Batch, 120 g fresh weight of cells/liter or 8 g dry weight/liter are obtained.

7 days after inoculation of the fermentor with the preculture of *Iris pallida*, the cell elicitor in the aqueous solution is introduced aseptically in the fermentor. The culture is maintained under the same conditions for 7 days.

b) Extraction of Dedifferentiated *Iris* Plant Cells Produced in a)

The culture was filtered through a nylon filter of porosity of 50 μm to retrieve the biomass and remove the conditioned culture medium.

The biomass is resuspended in reverse osmosis water in an amount equivalent to the starting culture.

The suspension is passed to High Pressure Homogenizer (HPH) on microfluidics to 1250 Bar, and then centrifuged at 6000 g for 20 min at 4° C., and filtered through GFD and GFF.

The final product is then frozen at −20° C. and lyophilized.

Between 2.5 and 3.5 g of extract/100 g of fresh cells are thus obtained, which is between 3 and 4 g/L of culture.

Example 3: Demonstration of the Eliciting Effect of *Lactobacillus delbrueckii*

This example shows that the use of an extract of *Lactobacillus delbrueckii* spp *lactis* makes it possible to induce the expression and secretion of a CGRP antagonist activity by dedifferentiated *iris* plant cells.

Materials and Methods

*Iris* extracts, prepared according to Example 2, put in contact or not with different doses of *Lactobacillus delbrueckii* spp *lactis* extracts prepared according to Example 1, were tested on HEK cell line stably transfected with the receiver hCALCRL and associated protein hRAMPI. This line expresses the reporter geneβ-lactamase under the control of the response element to the cyclic AMP (CRE).

Composition of the culture medium:

500 mL DMEM medium 4.5 g/L (Glucose)

50 ml serum dialyzed 12.5 ml Hepes (1 M)

5 mL of peni/Strepto/fungizone (100×)

Extracts were diluted extemporaneously before use in 1 ml of culture medium supplemented with 1% DMSO and 0.1% pluronic acid, at a concentration of 20 mg/ml initial.

For some samples, the solubilization was incomplete and was therefore scored visually:

"OK": total solubilization.

"Suspension": homogeneous mixture of small particles of the same size.

"Particulate": non-homogeneous mixture of particles of different sizes.

Cells were seeded the day before in 384-well plates and incubated at 37° C. and 5% $CO_2$.

After 24 hours, the cells were treated with the reference ligand CGRP to its EC80 (0.2 nM final) and the dose responses of the extracts to be tested. The extracts were prediluted in dose-response of 10 points to 2000 mcg mL final concentration for the first, and serial dilutions ¼.

After 3 hours incubation at 37° C. 5% $CO_2$, the substrate of β-lactamase was added.

After 2 hours incubation at room temperature, the plates were read with a spectrophotometer.

The data was normalized between 0% and 100% activity, thanks to the controls included in the plate. Dose-response curves were plotted using the XLfit software, the IC50s are expressed in μg/ml.

Results

Table 1 hereinbelow presents the results obtained.

TABLE 1

Antagonistic activity of CGRP expressed by the iris plant cells in contact with *L. delbrueckii*

| Source | Lot | Concentration *L. delbrueckii* | IC50 (μg/mL) | % inhibition | Solubilization |
|---|---|---|---|---|---|
| Medium conditioned | 1 | 0 | 75 | 96 | particulate |
| Medium conditioned | 2 | 0 | 10 | 94 | particulate |
| Medium conditioned | 1 | 0.1% | 35 | 97 | particulate |
| Medium conditioned | 2 | 0.1% | 1.8 | 112 | particulate |
| Medium conditioned | 1 | 0.15% | 30 | 104 | particulate |
| Medium conditioned | 2 | 0.15% | 39 | 95 | particulate |
| Medium conditioned | 1 | 0.20% | 2.7 | 97 | particulate |
| Medium conditioned | 2 | 0.20% | 1.1 | 90 | suspension |
| Pristine medium | | 0 | N/A | N/A | OK |
| Pristine medium | | 0.1% | N/A | N/A | OK |
| Pristine medium | | 0.15% | N/A | N/A | OK |
| Pristine medium | | 0.20% | N/A | N/A | OK |
| Dedifferenciated plant cells | 1 | 0 | 1.4 | 112 | particulate |
| Dedifferenciated plant cells | 2 | 0 | 2.9 | 105 | suspension |
| Dedifferenciated plant cells | 1 | 0.1% | 4.6 | 91 | suspension |
| Dedifferenciated plant cells | 2 | 0.1% | 4.1 | 97 | particulate |
| Dedifferenciated plant cells | 1 | 0.15% | 4.9 | 96 | suspension |
| Dedifferenciated plant cells | 2 | 0.15% | 5.6 | 105 | suspension |
| Dedifferenciated plant cells | 1 | 0.20% | 0.5 | 111 | particulate |
| Dedifferenciated plant cells | 2 | 0.20% | 0.6 | 107 | particulate |

The conditioned medium is a medium that has been in contact with the plant cells.

The pristine medium is the medium before seeding, which has not been in contact with the plant cells.

These results therefore show that the addition of *L. delbrueckii* at a concentration of 0.2% results in a gain in activity with respect to controls without elicitor. However, the elicitor *L. delbrueckii* alone has no activity.

Thus, the Applicant has developed a technique for elicitation for plant cells which allows for both intracellular production but also excretion of the antagonist active principle of CGRP extracellularly thereby increasing production yields by at least a factor of 2.

Example 4: Comparison of the Effectiveness of *Lactobacillus delbrueckii* Compared to Other Elicitors Materials and Methods Several "conventional" *iris* elicitors were tested: methyl jasmonate, chitin and alginate, as well as other "non-conventional" elicitors: $CaCl_2$, *Staphylococcus epidermidis, Lactobacillus delbrueckii*, β-D-glucan, $AlCl_3$ and $SrCl_2$.

All elicitors were tested at three concentrations and in triplicate on the dedifferentiated *iris* plant cells prepared according to Example 2.

The CGRP antagonist activity was measured as described in Example 3.

Results

Table 2 hereinbelow presents the results obtained.

TABLE 2

Antagonistic activity of CGRP expressed by the iris plant cells placed in contact with different elicitors

| Elicitor | Concentration | Source | % inhibition |
|---|---|---|---|
| — | — | Intracellular | 51 |
| — | — | Intracellular | 32 |
| Methyl-jasmonate | 20 mM | Intracellular | 57 |
| Methyl-jasmonate | 20 mM | Extracellular | 4 |

TABLE 2-continued

| Antagonistic activity of CGRP expressed by the iris plant cells placed in contact with different elicitors | | | |
|---|---|---|---|
| Elicitor | Concentration | Source | % inhibition |
| Methyl-jasmonate | 100 mM | Intracellular | 54 |
| Methyl-jasmonate | 100 mM | Extracellular | 5 |
| Methyl-jasmonate | 500 mM | Intracellular | 55 |
| Methyl-jasmonate | 500 mM | Extracellular | 0 |
| Chitin | 0.2 g/L | Intracellular | 57 |
| Chitin | 0.2 g/L | Extracellular | 10 |
| Chitin | 1 g/L | Intracellular | 42 |
| Chitin | 1 g/L | Extracellular | 12 |
| Chitin | 5 g/L | Intracellular | 37 |
| Chitin | 5 g/L | Extracellular | 0 |
| Alginate | 0.2 g/L | Intracellular | 60 |
| Alginate | 0.2 g/L | Extracellular | 39 |
| Alginate | 1 g/L | Intracellular | 53 |
| Alginate | 1 g/L | Extracellular | 61 |
| Alginate | 5 g/L | Intracellular | 61 |
| Alginate | 5 g/L | Extracellular | 16 |
| *S. epidermidis* | 0.20% | Intracellular | 54 |
| *S. epidermidis* | 0.20% | Extracellular | 9 |
| *S. epidermidis* | 1% | Intracellular | 50 |
| *S. epidermidis* | 1% | Extracellular | 14 |
| *S. epidermidis* | 5% | Intracellular | 50 |
| *S. epidermidis* | 5% | Extracellular | 16 |
| $CaCl_2$ | 0.20% | Intracellular | 42 |
| $CaCl_2$ | 0.20% | Extracellular | 57 |
| $CaCl_2$ | 1% | Intracellular | 49 |
| $CaCl_2$ | 1% | Extracellular | 68 |
| $CaCl_2$ | 5% | Intracellular | 69 |
| $CaCl_2$ | 5% | Extracellular | 70 |
| β-D-glucan | 0.2 g/L | Intracellular | 83 |
| β-D-glucan | 0.2 g/L | Extracellular | 1 |
| β-D-glucan | 0.8 g/L | Intracellular | 82 |
| β-D-glucan | 0.8 g/L | Extracellular | −1 |
| β-D-glucan | 2.25 g/L | Intracellular | 82 |
| β-D-glucan | 2.25 g/L | Extracellular | 0 |
| $SrCl_2$ | 0.69 mg/L | Intracellular | 79 |
| $SrCl_2$ | 0.69 mg/L | Extracellular | 0 |
| $SrCl_2$ | 69.9 mg/L | Intracellular | 79 |
| $SrCl_2$ | 69.9 mg/L | Extracellular | 1 |
| $SrCl_2$ | 699 mg/L | Intracellular | 80 |
| $SrCl_2$ | 699 mg/L | Extracellular | 1 |
| $SrCl_2$ | 6.99 g/L | Intracellular | 79 |
| $SrCl_2$ | 6.99 g/L | Extracellular | 7 |
| $AlCl_3$ | 0.024 g/L | Intracellular | 77 |
| $AlCl_3$ | 0.024 g/L | Extracellular | 1 |
| $AlCl_3$ | 0.121 g/L | Intracellular | 80 |
| $AlCl_3$ | 0.121 g/L | Extracellular | 2 |
| $AlCl_3$ | 0.603 g/L | Intracellular | 81 |
| $AlCl_3$ | 0.603 g/L | Extracellular | 26 |
| *L. delbrueckii* | 0.20% | Intracellular | 98 |
| *L. delbrueckii* | 0.20% | Extracellular | 97 |
| *L. delbrueckii* | 1% | Intracellular | 78 |
| *L. delbrueckii* | 1% | Extracellular | 86 |
| *L. delbrueckii* | 5% | Intracellular | 44 |
| *L. delbrueckii* | 5% | Extracellular | 75 |

Only the extract from *Lactobacillus delbrueckii* spp *lactis* elicitor acts as an elicitor: nearly 100% inhibition is observed. This is one of the rare elicitors that makes the culture medium very active (97% inhibition in equivalent dry matter). Finally, this elicitor is very active at the lowest concentration which is 0.2%.

Note that *S. epidermidis* is also a Gram-positive bacterium and that it has no effect on the *iris* culture.

The invention claimed is:

1. A composition having a CGRP antagonist activity of at least about 70% that is obtained by a method of preparation comprising the steps:

a) placing in contact, in a culture medium, plant cells from the *Iris* genus with *Lactobacillus delbrueckii* under conditions suitable for inducing the expression of a CGRP antagonist activity, b) optionally separating plant cells cultivated in step a) from the culture medium, and c) recovering a composition with CGRP antagonist activity of at least about 70%.

2. The composition according to claim 1 wherein the CGRP antagonist activity is about 100%.

3. A cosmetic or pharmaceutical composition comprising a composition having a CGRP antagonist activity of at least about 70% according to claim 1, and a cosmetically acceptable carrier or a pharmaceutically acceptable carrier, wherein the amount of the composition having a CGRP antagonist activity is from 0.001% to 20% by weight based upon the total weight of the cosmetic or pharmaceutical composition.

4. The cosmetic or pharmaceutical composition according to claim 3 wherein the CGRP antagonist activity is about 100%.

5. The cosmetic or pharmaceutical composition according to claim 3, being in the form of an emulsion and containing from 0.3% to 30% by weight of at least one emulsifier based upon the total weight of the cosmetic or pharmaceutical composition.

6. The cosmetic or pharmaceutical composition according to claim 3, being a cosmetic composition containing at least one additive selected from the group of hydrophilic or lipophilic gelling agents, preservatives, antioxidants, solvents, perfumes, bulking agents, filters, odor absorbers and dyes.

7. The cosmetic composition according to claim 6, wherein the amount of said at least one additive is from 0.01 to 10% by weight of the total weight of the cosmetic composition.

8. A composition having a CGRP antagonist activity of at least about 70% that is obtained by a method of preparation comprising the steps:

a) placing in contact, in a culture medium, dedifferentiated plant cells from the *Iris* genus with *Lactobacillus delbrueckii* under conditions suitable for inducing the expression of a CGRP antagonist activity, b) optionally separating plant cells cultivated in step a) from the culture medium, and c) recovering a composition with CGRP antagonist activity of at least about 70%.

9. The composition according to claim 8 wherein the CGRP antagonist activity is about 100%.

10. A composition having a CGRP antagonist activity of at least about 70% that is obtained by a method of preparation comprising the steps:

a) placing in contact, in a culture medium, plant cells from *Iris pallida* with *Lactobacillus delbrueckii* under conditions suitable for inducing the expression of a CGRP antagonist activity, b) optionally separating plant cells cultivated in step a) from the culture medium, and c) recovering a composition with CGRP antagonist activity of at least about 70%.

11. The composition according to claim 10 wherein the CGRP antagonist activity is about 100%.

12. A cosmetic or pharmaceutical composition comprising a composition having a CGRP antagonist activity according to claim 10, and a cosmetically acceptable carrier or a pharmaceutically acceptable carrier, wherein the amount of the composition having a CGRP antagonist activity is from 0.001% to 20% by weight based upon the total weight of the cosmetic or pharmaceutical composition.

13. The composition according to claim 12 wherein the CGRP antagonist activity is about 100%.

14. A method for preparing a composition having a CGRP antagonist activity of at least about 70% comprising the steps:

a) placing in contact, in a culture medium, plant cells of an Iridaceae with *Lactobacillus delbrueckii* under conditions suitable for inducing the expression of a CGRP antagonist activity, b) optionally separating plant cells cultivated in step a) from the culture medium, and c) recovering a composition with CGRP antagonist activity of at least about 70%.

15. A method for treating disorders associated with an excessive synthesis and/or release of CGRP, which comprises administering the composition having a CGRP antagonist activity according to claim 1 to a subject in need of the treatment of disorders associated with an excessive synthesis and/or release of CGRP.

16. The method according to claim 15, wherein said disorder associated with an excessive synthesis and/or release of CGRP is selected from the group consisting of eczema, prurigo and Rosacea.

17. A method for treating sensitive skin which comprises applying the cosmetic composition according to claim 3 to the sensitive skin.

18. A method for treating dandruff which comprises applying the cosmetic composition according to claim 3 to hair in need of an anti-dandruff treatment.

* * * * *